United States Patent
Knobloch et al.

(10) Patent No.: US 9,909,971 B2
(45) Date of Patent: Mar. 6, 2018

(54) AIRCRAFT AND PARTICULATE DETECTION METHOD

(71) Applicant: GE Aviation Systems LLC, Grand Rapids, MI (US)

(72) Inventors: Aaron Jay Knobloch, Guilderland, NY (US); Andrew Scott Kessie, Cincinnati, OH (US); Joseph Bernard Steffler, Grand Rapids, MI (US); Brian Jacob Loyal, Grand Rapids, MI (US)

(73) Assignee: GE AVIATION SYSTEMS LLC, Grand Rapids, MI (US)

( * ) Notice: Subject to any disclaimer, the term of this patent is extended or adjusted under 35 U.S.C. 154(b) by 14 days.

(21) Appl. No.: 14/916,757

(22) PCT Filed: Sep. 6, 2013

(86) PCT No.: PCT/US2013/058419
§ 371 (c)(1),
(2) Date: Mar. 4, 2016

(87) PCT Pub. No.: WO2015/034513
PCT Pub. Date: Mar. 12, 2015

(65) Prior Publication Data
US 2016/0202168 A1      Jul. 14, 2016

(51) Int. Cl.
*G01N 15/10* (2006.01)
*G01N 15/06* (2006.01)
(Continued)

(52) U.S. Cl.
CPC ......... *G01N 15/0656* (2013.01); *B64D 45/00* (2013.01); *F02C 7/05* (2013.01);
(Continued)

(58) Field of Classification Search
CPC .................................. B64F 5/00; G01M 15/14
See application file for complete search history.

(56) References Cited

U.S. PATENT DOCUMENTS

| 4,528,844 A | 7/1985 | Couch |
| 4,625,280 A | 11/1986 | Couch |

(Continued)

FOREIGN PATENT DOCUMENTS

| CA | 2516958 A1 | 2/2006 |
| EP | 0120087 B1 | 1/1988 |

(Continued)

OTHER PUBLICATIONS

PCT Search Report and Written Opinion issued in connection with corresponding PCT Application No. PCT/US2013/058419 dated May 19, 2014.

(Continued)

*Primary Examiner* — Alex C Dunn
(74) *Attorney, Agent, or Firm* — GE Global Patent Operation; William S. Munnerlyn

(57) ABSTRACT

An aircraft including a jet engine including a core having a compressor and combustion chamber, and a particulate sensor located within the core and a particulate detection method for an aircraft having a jet engine where the method includes sensing particulates within the core and providing a corresponding value for the sensed particulates and providing an indication related thereto.

18 Claims, 3 Drawing Sheets

(51) Int. Cl.
  *G01C 21/20* (2006.01)
  *B64D 45/00* (2006.01)
  *F02C 7/05* (2006.01)
  *G01N 15/00* (2006.01)
(52) U.S. Cl.
  CPC ............ *G01C 21/20* (2013.01); *G01N 15/06* (2013.01); *B64D 2045/009* (2013.01); *B64D 2045/0085* (2013.01); *F05D 2260/80* (2013.01); *G01N 2015/0046* (2013.01)

(56) References Cited

U.S. PATENT DOCUMENTS

| | | | |
|---|---|---|---|
| 5,602,543 | A | 2/1997 | Prata et al. |
| 8,459,103 | B2 | 6/2013 | Khibnik et al. |
| 2009/0112519 | A1 | 4/2009 | Novis et al. |
| 2010/0073173 | A1* | 3/2010 | Zindy .................... G01N 15/06 340/627 |
| 2010/0313639 | A1 | 12/2010 | Khibnik et al. |
| 2011/0062973 | A1 | 3/2011 | Paterson |
| 2011/0179763 | A1 | 7/2011 | Rajamani |
| 2012/0068862 | A1 | 3/2012 | Tillitson |
| 2012/0324987 | A1* | 12/2012 | Khibnik .................. F02C 7/052 73/112.01 |
| 2013/0025348 | A1 | 1/2013 | Rajamani |
| 2013/0046507 | A1 | 2/2013 | Vega Paez et al. |
| 2013/0186269 | A1* | 7/2013 | Cheng ................. B01D 53/228 95/47 |
| 2013/0193978 | A1 | 8/2013 | Woolley et al. |
| 2013/0197739 | A1* | 8/2013 | Gallagher ................ B64F 5/60 701/31.5 |
| 2014/0007591 | A1* | 1/2014 | Khibnik .................... F02C 7/00 60/805 |
| 2014/0053629 | A1* | 2/2014 | Cahill ................ G01N 33/0063 73/28.01 |
| 2014/0157872 | A1* | 6/2014 | Welland ............. G01N 15/0656 73/28.02 |
| 2014/0233017 | A1* | 8/2014 | Hariram ............. G01N 15/1031 356/72 |

FOREIGN PATENT DOCUMENTS

| | | |
|---|---|---|
| EP | 253199 A2 | 1/1988 |
| EP | 1978222 A2 | 10/2008 |
| EP | 2538199 A2 | 12/2012 |
| EP | 2551660 A2 | 1/2013 |
| GB | 2482480 A | 2/2012 |
| JP | 2013044326 A | 3/2013 |
| WO | 2011151462 A1 | 12/2011 |

OTHER PUBLICATIONS

Unofficial English Translation of Chinese Office Action issued in connection with corresponding CN Application No. 201380079384.4 dated Sep. 5, 2016.

International Search Report and Written Opinion issued in connection with corresponding international application PCT/US2013/058419 dated May 19, 2014.

Unofficial English Translation of Japanese Office Action issued in connection with corresponding JP Application No. 2016540858 dated Jun. 6, 2017.

* cited by examiner

AIRCRAFT AND PARTICULATE DETECTION METHOD

BACKGROUND

Contemporary aircraft may include engines to provide propulsion for the aircraft. Such engines may ingest various types of particulate matter such as ash, sand, dust, dirt, gravel, and pollutants, which may negatively affect engine performance, the time the engine is on the wing of the aircraft (TOW), and subsequent overhaul cost. Harsh environments of the Middle East, Africa, India, and China, for example, can have a significant impact on engine TOW and hardware scrap/repair rates.

BRIEF DESCRIPTION

Embodiments of the innovation relate to a particulate detection method for an aircraft having a jet engine comprising a core, the method includes sensing particulates ingested into the core and providing a corresponding particulate value for the sensed particulates, selecting a particulate reference value, comparing the particulate value to the particulate reference value, and providing an indication based on the comparison.

In another aspect, an embodiment of the innovation relates to an aircraft having a jet engine having a core having a compressor and combustion chamber downstream of the compressor, a single button particulate sensor located within the core and configured to output a signal indicative of sensed particulates in a limited portion of the core, and a controller having a processor to process the sensor signal indicative of sensed particulates and determine a corresponding particulate value for the sensed particulates and configured to provide an indication regarding the sensed particulates.

DETAILED DESCRIPTION

Figure 1:
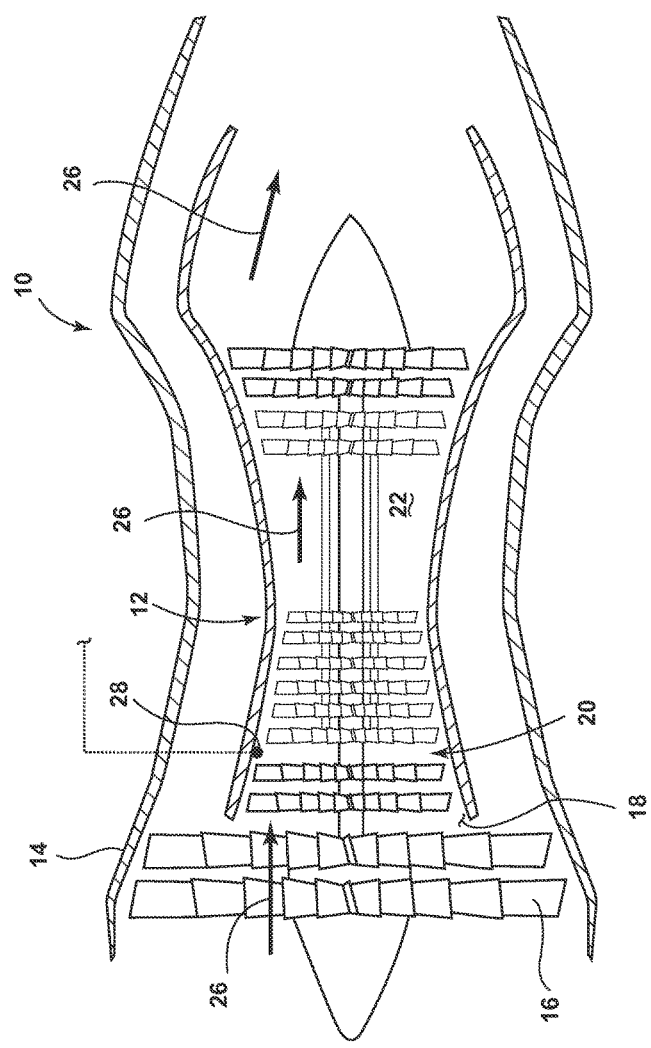
FIG. 1 is a schematic view of a jet engine assembly.

FIG. 1 schematically depicts a jet engine assembly 10 having a core 12, portions of which may be surrounded by a nacelle 14. The core 12 does not include the nacelle 14 and fan 16 of the jet engine assembly 10. The core 12 may include, among other things, an air intake 18, a compressor 20, and a combustion chamber 22 downstream from the compressor 20. Air may enter the air intake 18 and may be compressed in the compressor 20. Air may then be forced into the combustion chamber 22 where fuel is sprayed into it and the mixture of air and fuel may be ignited. Gases that form expand rapidly and are exhausted through the rear of the combustion chamber 22. Such an engine flow path is illustrated with arrows 26.

A particulate sensor 28 may be located within the core 12 and may be configured to output a signal indicative of sensed particles or particulates in a limited portion of the core 12. The particulate sensor 28 may be located within any suitable part of the core 12 in the engine flow path in a location where the incoming particulates are detectable. For example, the particulate sensor 28 may be located on a wall near the air intake, the booster section of the core 12, or within a low-pressure or high-pressure portion of the compressor 20, likely within the forward stages of the compressor 20. The particulate sensor 28 may be any suitable type of sensor including an electrostatic sensor, a lidar sensor, an optical sensor, etc. One sensor may be interchangeable with the others to provide multiple options for detecting different particulate in different regions of the world. By way of non-limiting examples, the particulate sensor 28 may be a plug or single button style sensor, an embedded ring, or patch sensor. Further, alternate electromagnetic sensor styles may be used to measure the charge on particulate matter. The particulate sensor 28 may provide an output indicative of a relative density and overall quantity of particulate being ingested by the jet engine assembly.

Figure 2:
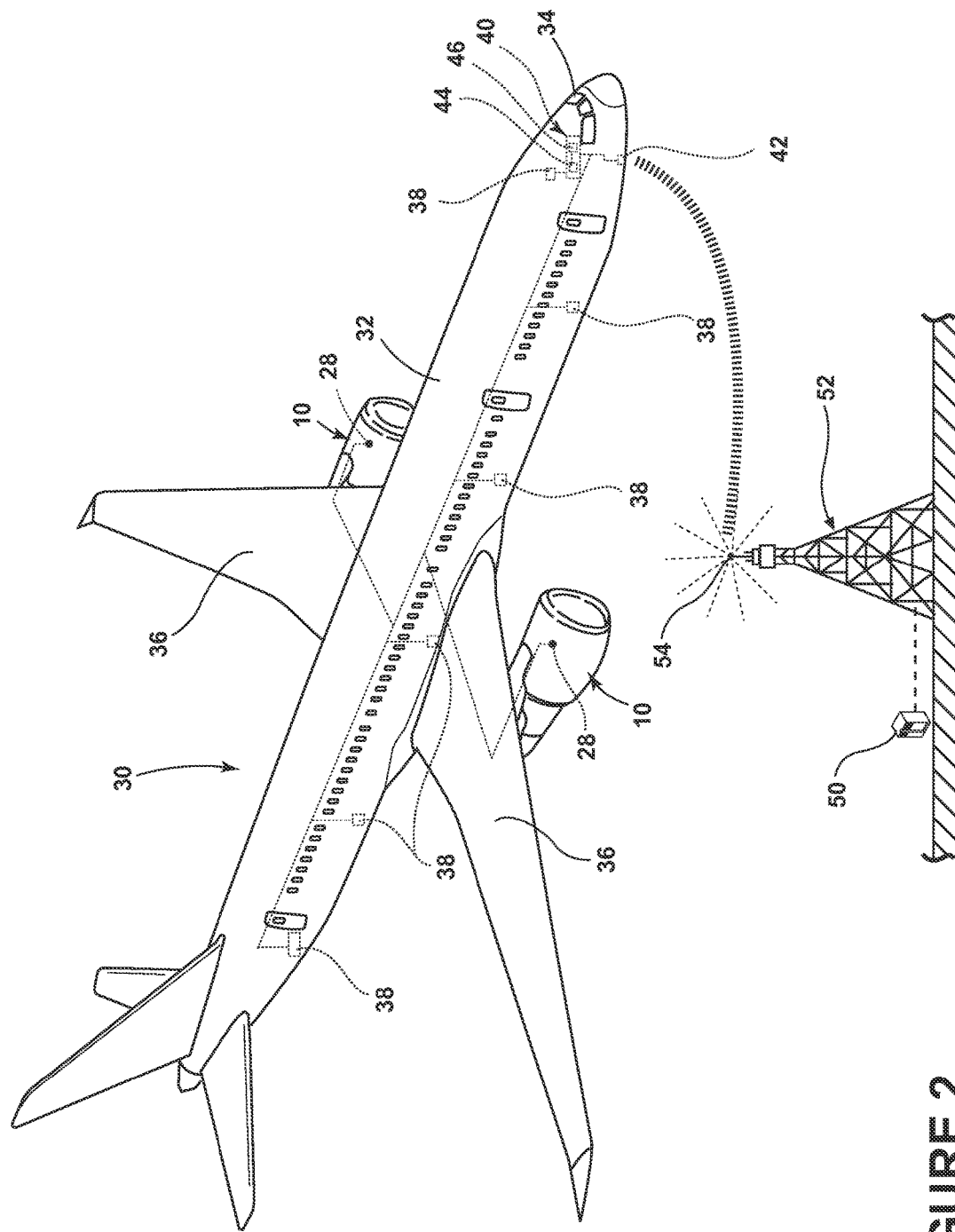
FIG. 2 is a perspective view of an aircraft including multiple jet engines, as shown in FIG. 1, and a ground system in which embodiments of the innovation may be implemented.

FIG. 2 illustrates an aircraft 30 that may execute embodiments of the innovation and may include one or more jet engine assemblies 10 as described above. A fuselage 32 may form a portion of the aircraft 30. A cockpit 34 may be positioned in the fuselage 32, and wing assemblies 36 may extend outward from the fuselage 32. A plurality of additional aircraft systems 38 that enable proper operation of the aircraft 30 may also be included in the aircraft 30 as well as a computer or controller 40 and a communication system having a wireless communication link 42. The additional aircraft systems 38 may include various navigational tools including an inertial reference system (IRS), altimeter, and/or global positioning system (GPS). The IRS may be an on-board system that senses the movement of the aircraft 30, and continuously calculates the aircraft's position, altitude, speed etc. The GPS may be installed on the aircraft 30 and gives position reports over a satellite and/or cellular network including a report of information such as speed, bearing, and altitude.

The controller 40 may be operably coupled to the plurality of aircraft systems 38 including the jet engine assemblies 10 and the particulate sensor 28. The controller 40 may also be connected with other controllers of the aircraft 30. The controller 40 may include memory 44, the memory 44 may include random access memory (RAM), read-only memory (ROM), flash memory, or one or more different types of portable electronic memory, such as discs, DVDs, CD-ROMs, etc., or any suitable combination of these types of memory. The controller 40 may include one or more processors 46, which may be running any suitable programs.

A computer searchable database of information may be stored in the memory 44 and accessible by the processor 46. The processor 46 may run a set of executable instructions to display the database or access the database. Alternatively, the controller 40 may be operably coupled to a database of information. For example, such a database may be stored on an alternative computer or controller. It will be understood that the database may be any suitable database, including a single database having multiple sets of data, multiple discrete databases linked together, or even a simple table of data. It is contemplated that the database may incorporate a number of databases or that the database may actually be a number of separate databases.

Alternatively, it is contemplated that the database may be separate from the controller 40 but may be in communication with the controller 40 such that it may be accessed or queried by the controller 40. For example, it is contemplated that the database may be contained on a portable memory device and in such a case, the aircraft 30 may include a port for receiving the portable memory device and such a port would be in electronic communication with the controller 40 such that the controller 40 may be able to read the contents of the portable memory device. It is also contemplated that the database may be updated through the wireless communication link 42 and that in this manner, real time information such as information regarding historical fleet wide data may be included in the database and may be accessed by the controller 40.

Further, it is contemplated that such a database may be located off the aircraft 30 at a location such as airline operation center, flight operations department control, or another location. The controller 40 may be operably coupled to a wireless network over which the database information may be provided to the controller 40.

The database may store data that may include geographic position data, altitude data, etc. The database may also include reference values including particulate reference values, including particulate reference values related to geographic position and/or altitude positions and comparison threshold values related to the particulate reference values.

It will be understood that while the controller 40 has been shown near a cockpit 34 of the aircraft 30 that the controller 40 may alternatively be located on the jet engine assembly 10 or may be a part of the Full Authority Digital Engine Controls for the engine or a part of a health management system. In such an instance information from the additional aircraft systems 38 and the database may be utilized by the controller 40 regardless of where the controller 40 is located or which systems it is a part of.

Further, while a commercial aircraft has been illustrated, it is contemplated that all or portions of the embodiments of the innovation may be implemented on non-commercial aircraft and not in an aircraft, including in a computer 50 at a ground system 52. Furthermore, database(s) as described above may also be located in a destination server or a computer 50, which may be located at and include the designated ground system 52. Alternatively, the database may be located at an alternative ground location. The ground system 52 may communicate with other devices including the controller 40 and databases located remote from the computer 50 via a wireless communication link 54. The ground system 52 may be any type of communicating ground system 52 such as an airline control or flight operations department.

For example, the controller 40 and/or the computer 50 may include all or a portion of a computer program having an executable instruction set for providing a particulate value based on the sensed particulates and determining whether such a particulate value satisfies a particulate reference value such that an indication may be provided based thereon. Regardless of whether the controller 40 and/or the computer 50 runs the program, the program may include a computer program product that may include machine-readable media for carrying or having machine-executable instructions or data structures stored thereon. Such machine-readable media may be any available media, which can be accessed by a general purpose or special purpose computer or other machine with a processor. Generally, such a computer program may include routines, programs, objects, components, data structures, algorithms, etc. that have the technical effect of performing particular tasks or implementing particular abstract data types. Machine-executable instructions, associated data structures, and programs represent examples of program code for executing the exchange of information as disclosed herein. Machine-executable instructions may include, for example, instructions and data, which cause a general purpose computer, special purpose computer, or special purpose processing machine to perform a certain function or group of functions. It will be understood that the wireless communication link 42 and the wireless communication link 54 may both be utilized to transmit data such that the particulates may be detected by either the controller 40 and/or the computer 50.

It will be understood that the aircraft 30 and computer 50 merely represent two exemplary embodiments that may be configured to implement embodiments or portions of embodiments of the innovation. During operation, either the aircraft 30 and/or the computer 50 may compare the particulate value with the particulate reference value to determine if an indication should be provided. By way of non-limiting example, while the aircraft 30 is being operated the particulate sensor 28 may provide electronic output related to particulates within the core. The output from the particulate sensor 28 may be digitally processed to determine the relative density and overall quantity of particulate being ingested. The controller 40 and/or the computer 50 may also utilize inputs from a variety of the additional aircraft systems 38, the database(s), and/or information from airline control or flight operations department. By way of non-limiting example, the controller 40 and/or the computer 50 may analyze data output from the IRS and/or GPS and determine a particulate reference values based thereon. It is contemplated that the particulate reference values may be determined in any suitable manner including that they may be defined through product design or may be based on historical values related to the determined location of the aircraft. Further, the controller 40 and/or the computer 50 may analyze the data output by the particulate sensors 28. Based on the comparison of the particulate value with the particulate reference value an indication may be provided to alert the pilots and/or Airline Operations Control to potentially harmful concentrations of particulate from volcanic ash clouds, dust storms, or nearby airborne construction debris. Alternately, such data may be recorded and stored on a remote diagnostics storage system of the aircraft for immediate and/or future use. In this manner, the environmental impact on the engine may be quantified as flight-by-flight particulate data may be gathered and utilized.

Figure 3:
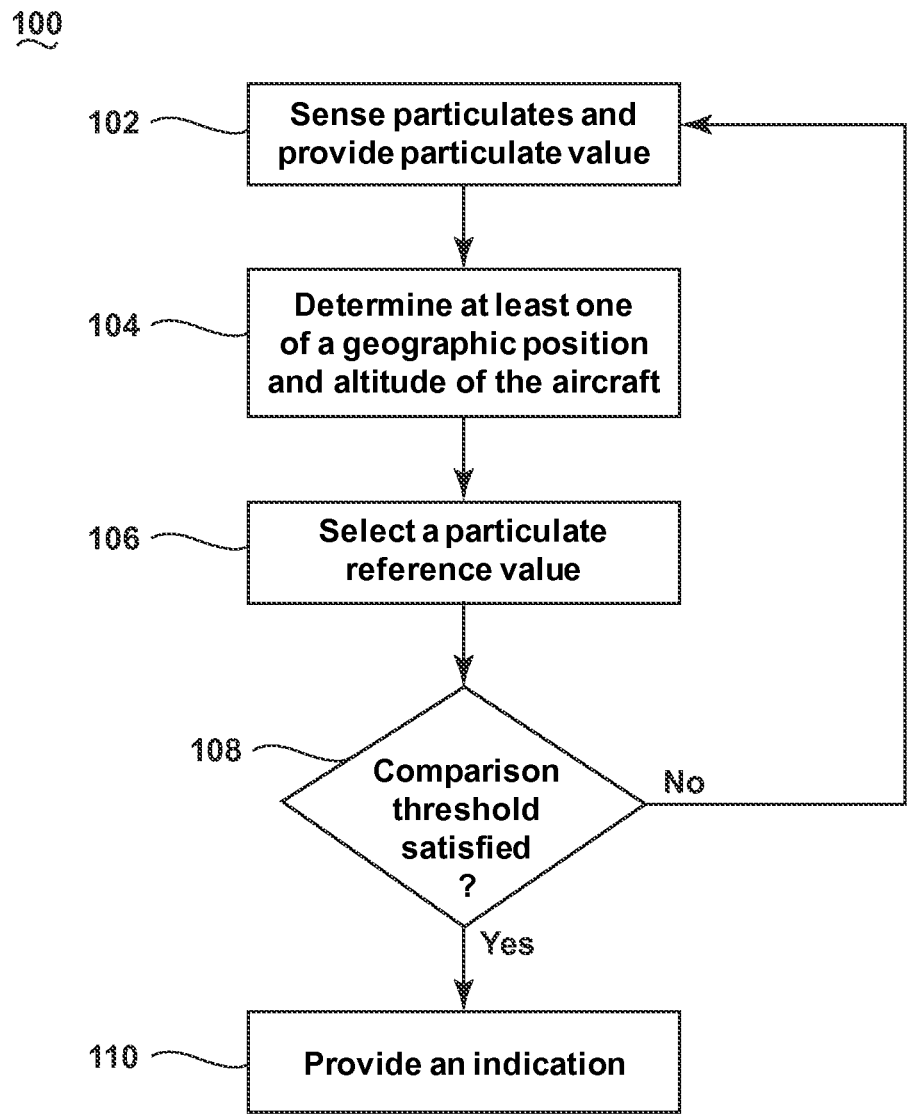
FIG. 3 is a flowchart showing a method or particulate detection according to an embodiment of the innovation.

In accordance with an embodiment of the innovation, FIG. 3 illustrates a method 100, which may be used to detect particulates. The method 100 begins at 102 by sensing particulates within the core 12 of the jet engine assembly 10. This may include receiving data from one or more of the particulate sensors 28. It will be understood that the sensing may be conducted with an electrostatic, laser, radar or optical sensor or other suitable particulate sensor 28 configured to output a signal indicative of sensed particulates in a limited portion of the core 12. The data may be sensed during a number of different regimes. For example, the data may be sensed during the entire flight, or segments of the flight, such as during taxi, cruise, takeoff, decent, landing, etc. It is contemplated that the sensed data may be raw aircraft data from which a variety of other information may be derived or otherwise extracted. It will be understood that regardless of whether the data is sensed directly or derived from sensed data, the data may still be considered to be sensed data. At 102, a corresponding particulate value may be determined and provided based on the sensed particulates. It is contemplated that the particulate sensor 28 may be configured to provide the particulate value and that the controller 40 and/or computer 50 may be configured to provide the particulate value based on the output from the particulate sensor 28.

At 104, at least one of a geographic position and altitude of the aircraft (30), corresponding to the sensing of the particulates, may be determined. This may include the controller 40 and/or computer 50 determining at least the geographic position of the aircraft when the particulates were sensed. Such information may be determined based on the IRS, GPS, etc. For example, a GPS coordinate may be recorded from a GPS device located on the aircraft 30 and the controller 40 and/or computer 50 may determine a geographical position based thereon. This may alternatively include the controller 40 and/or computer 50 determining the altitude or both the geographic position and the altitude of the aircraft when the particulates were sensed. In such an instance where both are determined, determining the geographic position may include the controller 40 and/or computer 50 determining a GPS coordinate from a GPS device on the aircraft 30 and the controller 40 and/or computer 50 determining the altitude may include determining an altitude from an altimeter on the aircraft 30 or from the IRS.

At 106, a particulate reference value may be selected by the controller 40 and/or computer 50. The particulate reference value may be selected based on the geographic position and/or the altitude determined at 104. The reference value may also be the maximum allowable for any geographical location. The reference value may also be selected based on the season or other variations in the weather. Selecting the particulate reference value may be done in a variety of manners including by the controller 40 and/or computer 50 conducting a query of a database of reference values. This may include the controller 40 and/or computer 50 querying a database that is on a computer or other device aboard the aircraft 30 or querying a database at the ground system 52. In this manner, a particulate reference value correlating to where the particulates were sensed may be determined. It is also contemplated that the particulate reference value may be a running average of a predetermined number of prior particulate values for the determined geographic position and/or the determined altitude.

At 108, the particulate value may be compared to the particulate reference value. For example, the comparison may include taking a difference between the particulate value and the particulate reference value. It may also be determined whether a comparison threshold has been satisfied. The comparison threshold may be absolute or may vary based on the determined geographic position and/or the determined altitude. The comparison threshold value may also be obtained by the controller 40 and/or the computer 50 conducting a query of a database of reference values. The term "satisfies" the threshold is used herein to mean that the variation comparison satisfies the predetermined threshold, such as being equal to, less than, or greater than the threshold value. It will be understood that such a determination may easily be altered to be satisfied by a positive/negative comparison or a true/false comparison. For example, a less than threshold value can easily be satisfied by applying a greater than test when the data is numerically inverted. In the case where the comparison may include taking a difference between the particulate value and the particulate reference value, satisfying the comparison threshold may include the absolute value of the difference being equal to or greater than the comparison threshold.

In implementation, the particulate reference values and comparisons may be converted to an algorithm. Such an algorithm may be converted to a computer program comprising a set of executable instructions, which may be executed by the controller 40 and/or the computer 50. In this manner, the controller 40 and/or the computer 50 may determine if the results of the comparison are acceptable and if an indication based on the sensed particulates should be provided.

At 110, an indication may be provided based on the comparison. With respect to the illustrated method 100, this may include that an indication may be provided when the comparison indicates the satisfying of the comparison threshold. For example, the controller 40 and/or the computer 50 may provide an indication that the sensed particulates have exceeded the relevant threshold. The indication may be provided in any suitable manner at any suitable location including on a flight deck of the aircraft 30, such as on a primary flight display, and/or on a display at the ground system 52. For example, if the controller 40 ran the program, then the suitable indication may be provided on the aircraft 30 and/or may be uploaded to the ground system 52. Alternatively, if the computer 50 ran the program, then the indication may be uploaded or otherwise relayed to the aircraft 30. Alternatively, the indication may be relayed such that it may be provided at another location such as an airline control or flight operations department.

It will be understood that the particulate detection method 100 illustrated is merely for illustrative purposes. For example, the sequence of steps depicted is for illustrative purposes only, and is not meant to limit the method 100 in any way as it is understood that the steps may proceed in a different logical order or additional or intervening steps may be included without detracting from embodiments of the innovation. By way of non-limiting example, the method 100 may alternatively include comparing the particulate value to the particulate reference value and if the particulate value satisfies the particulate reference value and indication may be provided. It will be understood that the various thresholds are all configurable.

Further, it may also be possible for the controller 40 and/or computer 50 to determine a variety of events from the particulate data. For example, the particulate sensor 28 may double as a hail and/or rain detector for improving engine operability and performance, especially on decent where some aviation engines must currently assume the presences of rain and/or hail. The particulate value may provide an indication of any number of events and allow for better determination of seasonal variation, transient events, ash clouds, rain, hail, airport construction, pollution, etc. The sensor signal from the particulate sensor 28 may be analyzed, by the controller 40 and/or the computer 50, along with other aircraft data to give context to the sensor signal to allow the controller 40 and/or the computer 50 to differentiate between events. Further, certain characteristics in the sensor signal itself may provide characteristics to aid in differentiate between events. It is also contemplated that various indications may be provided regarding such determined ash clouds, ice, and/or dust storms. For example, the particulate data may be linked to the altitude data and the controller 40 and/or the computer 50 may determine an ash cloud based on the particulate data and the height the aircraft 30 is flying at and may provide an appropriate indication based thereon. An indication, or lack of indication, of hail and/or rain could be used by the engine control system along with other key sensors and algorithms to improve engine operability during key flight operations culminating in improved performance, safety, and fuel consumption.

Technical effects of the above described embodiments include that data gathered by the aircraft during flight may be utilized to detect particulate matter ingested into the engine and may allow for a size and quantity of particulates ingested to be determined. Such information may be invaluable to further understanding, and ultimately reducing, the impact of harsh environments on aviation engines. The particulate information may allow for improved health management capability using both long and short term particulate sensor data. Allowing for improved maintenance and cleaning that may result in better TOW, fewer unscheduled engine removals, and better overhaul shop scheduling. This allows for cost savings by reducing maintenance cost, rescheduling cost, and minimizing operational impacts including minimizing the time aircraft are grounded. The embodiments described above may also provide more accurate particulate information regarding particulate ingestion in the engine as compared to sensors located in a region where air bypasses the core. Such information may be used to change a schedule of the aircraft including when maintenance and/or inspections may occur.

This written description uses examples to disclose the innovation, including the best mode, and also to enable any person skilled in the art to practice the innovation, including making and using any devices or systems and performing any incorporated methods. The patentable scope of the innovation is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A particulate detection method for an aircraft having a jet engine comprising a core having a compressor and a combustion chamber, the method comprising:
   sensing particulates within the core and providing a corresponding particulate value for the sensed particulates;
   determining at least one of a geographic position and altitude of the aircraft corresponding to the sensing of the particulates;
   selecting a particulate reference value for the determined at least one of the geographic position and altitude;
   comparing the particulate value to the particulate reference value; and
   providing an indication based on the comparison,
   wherein providing an indication based on the comparison further comprises providing the indication to a computer aboard the aircraft, providing an alert on a flight deck of the aircraft and providing an indication to one or more ground systems, and
   wherein sensing particulates further comprises sensing particulates during at least one of taxi, takeoff, descent, and landing, but not sensing particulates during cruise.

2. The method of claim 1 wherein the particulate sensing occurs within forward stages of the compressor.

3. The method of claim 2 wherein the particulate sensing comprises sensing using one particulate sensor.

4. The method of claim 1 wherein the particulate sensing is conducted with an electrostatic sensor.

5. The method of claim 1 wherein the determining at least one of the geographic position and the altitude comprises determining at least the geographic position.

6. The method of claim 1 wherein the determining at least one of the geographic position and the altitude comprises determining both the geographic position and the altitude.

7. The method of claim 6 wherein the determining the geographic position comprises determining a GPS coordinate from a GPS device on the aircraft and determining the altitude comprises determining an altitude from an altimeter on the aircraft.

8. The method of claim 1 wherein the selecting the particulate reference value comprises conducting a query of a database of reference values on a computer aboard the aircraft.

9. The method of claim 8 wherein the providing an indication comprises providing an alert on a flight deck of the aircraft.

10. The method of claim 1 wherein the comparing comprises taking a difference between the particulate value and the particulate reference value.

11. The method of claim 10 wherein providing an indication comprises when the comparison indicates a satisfying of a comparison threshold.

12. The method of claim 11 wherein the satisfying the comparison threshold comprises determining the absolute value of the difference being equal to or greater than the comparison threshold.

13. The method of claim 1 wherein the particulate reference value is a running average of a predetermined number of prior particulate values.

14. An aircraft, comprising:
   a jet engine assembly, comprising:
      a core having a compressor and a combustion chamber downstream of the compressor; and
      a single button particulate sensor located within the core and configured to output a signal indicative of sensed particulates in a limited portion of the core; and
      a controller having a processor to process the sensor signal indicative of sensed particulates and determine a corresponding particulate value for the sensed particulates and configured to provide an indication regarding the sensed particulates,
      wherein the single button particulate sensor senses particulates during at least one of taxi, takeoff, descent, and landing, but not during cruise.

15. The aircraft of claim 14 wherein the controller is further configured to determine at least one of a geographic position and altitude of the aircraft corresponding to the sensing of the particulates, select a particulate reference value for the determined at least one of a geographic position and altitude, compare the particulate value to the particulate reference value, and provide an indication when the comparison indicates the satisfying of a comparison threshold.

16. A particulate detection method for an aircraft having a jet engine, the jet engine comprising a core, the core comprising a compressor and a combustion chamber, the method comprising:
   sensing particulates within the core and providing a corresponding particulate value for the sensed particulates;
   determining at least one of a geographic position and altitude of the aircraft corresponding to the sensing of the particulates;
   selecting a particulate reference value for the determined at least one of the geographic position and altitude;
   comparing the particulate value to the particulate reference value; and
   alerting a pilot of potentially harmful concentrations of particulate,
   wherein sensing particulates further comprises sensing particulates during at least one of taxi, takeoff, descent, and landing, but not sensing particulates during cruise.

17. The method of claim 1 wherein sensing particulates within the core comprises sensing particulates within the core of a jet engine comprising a core having a compressor and a combustion chamber.

18. The method of claim 1 wherein selecting a particulate reference value further comprises accessing a computer-searchable database of information, the computer-searchable database of information including memory and one or more processors.

* * * * *